United States Patent [19]

Deflandre et al.

[11] Patent Number: 5,624,663
[45] Date of Patent: Apr. 29, 1997

[54] PHOTOSTABLE COSMETIC FILTER COMPOSITION COTAINING A UV-A FILTER AND A SUBSTITUTED DIALKYLBENZALMALONATE, THE USE OF SUBSTITUTED DIALKYLBENZALMALONATES IN COSMETICS AS BROAD-BAND SOLAR FILTERS AND NOVEL SUBSTITUTED DIALKYL MALONATES

[75] Inventors: Andre Deflandre, Orry la Ville; Serge Forestier, Claye-Souilly; Gerard Lang, Saint-Gratien; Herve Richard; Madeleine Leduc, both of Paris, all of France

[73] Assignee: L'Oreal, Paris, France

[21] Appl. No.: 476,095

[22] Filed: Jun. 7, 1995

Related U.S. Application Data

[63] Continuation of Ser. No. 677,376, Mar. 27, 1991, which is a continuation of Ser. No. 236,645, Aug. 25, 1988, abandoned.

[30] Foreign Application Priority Data

Aug. 28, 1987 [FR] France .................. 87 12047

[51] Int. Cl.$^6$ .............. A61K 7/42; A61K 7/40; A61K 31/12
[52] U.S. Cl. .................. 424/59; 514/685; 568/304
[58] Field of Search .............. 424/59; 514/685; 568/304

[56] References Cited

U.S. PATENT DOCUMENTS

| 3,160,665 | 12/1964 | Shegrist et al. | 424/59 |
| 3,256,312 | 6/1966 | Strobel et al. | 424/59 |
| 3,336,357 | 8/1967 | Strobel et al. | 424/59 |
| 4,322,455 | 3/1982 | Olson et al. | 427/160 |
| 4,387,089 | 6/1983 | DePolo | 424/59 |
| 4,524,165 | 6/1985 | Musser et al. | 524/99 |

FOREIGN PATENT DOCUMENTS

| 0005182 | 11/1979 | European Pat. Off. | 424/59 |
| 0100651 | 2/1984 | European Pat. Off. | 424/59 |
| 7510873 | 9/1974 | Netherlands | 424/59 |
| 2134390 | 8/1984 | United Kingdom | 424/59 |

OTHER PUBLICATIONS

Chemical Abstracts, vol. 75, 1971, p. 327, No. 48636n, Columbus, Ohio. Avetisyan et al.: "Derivatives of dibasic carboxylic acids. XXXIV: N–Methyl–alpha–(p–Alkoxyphenyl)succinimides".

Chemical Abstracts, vol. 83, 1975, p. 507, No. 113874v, Columbus, Ohio. Bhatt et al.: "Preparation of optically active benzylidenes by the Knoevenagel reaction (+)–di(2–methylbutyl)malonate".

Primary Examiner—Shelley A. Dodson
Attorney, Agent, or Firm—Marshall, O'Toole, Gerstein, Murray & Borun

[57] ABSTRACT

A photostable cosmetic filter composition for protecting human skin against UV radiation at wavelengths between 280 and 380 nm comprises, in a cosmetically acceptable support medium containing at least one oily phase, 1 to 3% by weight of a dibenzoylmethane derivative and at least 1% by weight of a substituted dialkylbenzalmalonate having formula I:

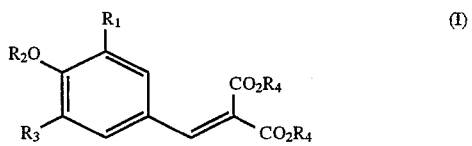

$R_1$ and $R_3$ may be identical or different and represent H or a straight- or branched-chain $C_1$–$C_8$ alkoxy radical.

$R_2$ and $R_4$ represent a straight- or branched-chain $C_1$–$C_8$ alkyl radical.

The molar ratio of compound (I) to the dibenzoylmethane derivative is greater than or equal to 0.6.

11 Claims, No Drawings

PHOTOSTABLE COSMETIC FILTER COMPOSITION COTAINING A UV-A FILTER AND A SUBSTITUTED DIALKYLBENZALMALONATE, THE USE OF SUBSTITUTED DIALKYLBENZALMALONATES IN COSMETICS AS BROAD-BAND SOLAR FILTERS AND NOVEL SUBSTITUTED DIALKYL MALONATES

This application is a continuation of application Ser. No. 07/677,376, filed Mar. 27, 1991, which is a continuation of application Ser. No. 07/236,645, filed Aug. 25, 1988, abandoned.

BACKGROUND OF THE INVENTION

The present invention relates to a photostable cosmetic composition for the protection of skin against UV radiation comprising in combination a UV-A filter and a substituted dialkylbenzalmalonate. It also relates to the use of this composition in protecting skin against UV radiation, to a method of stabilizing a UV-A filter by the substituted dialkylbenzalmalonate, to the use of substituted dialkylbenzalmalonates as broad-band solar filters and to novel substituted dialkylbenzalmalonates.

Light at wavelengths between 280 nm and 400 nm is known to brown human skin and light at wavelengths between 280 and 320 nm, known as UV-B, produce erythemas and cutaneous burns which may hinder tan development; the UV-B radiation must therefore be filtered out.

It is also known that UV-A radiation at wavelengths between 320 and 400 nm and producing browning of the skin can damage the skin, especially when it is sensitive or continually exposed to the sun's rays. UV-A radiation produces, in particular, loss of skin elasticity and the appearance of wrinkles leading to premature ageing. It favors the start of the erythematous reaction or, in some subjects, amplifies the same and may even trigger phototoxic or photoallergic reactions. Thus it is also desirable to filter out UV-A radiation.

French patents FR 2 326 405 and FR 2 440 933 and European patent EP 114 607 describe dibenzoylmethane derivatives as UV-A filters. The patents propose combining these UV-A filters with various UV-B filters to absorb all UV radiation at wavelengths between 280 and 380 nm. Among the UV-B filters used in combination with these dibenzoylmethane derivatives are paramethoxycinnamic acid esters, in particular 2-ethylhexyl paramethoxycinnamate, sold by GIVAUDAN under the trade name "PARSOL MCX".

Unfortunately, when used in combination with this UV-B filter, the dibenzoylmethane derivatives described in the aforementioned patents are not sufficiently photochemically stable to be able to provide constant protection during prolonged exposure to the sun. This necessitates repeated applications at regular and frequent intervals in order to obtain effective skin protection against UV radiation.

SUMMARY OF THE INVENTION

It has been discovered that combination of dibenzoylmethane derivatives as described above with a substituted dialkylbenzalmalonate having general formula (I)

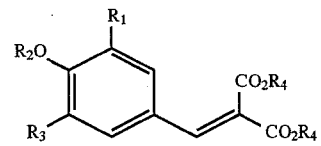

in well defined proportions and molar ratios surprisingly results in remarkable photochemical stability of the dibenzoylmethane derivatives.

In general formula (I) substituents $R_1$ to $R_4$ may have the following meanings:

$R_1$ and $R_3$ may be identical or different and represent a hydrogen atom or a $C_1$–$C_8$ straight- or branched-chain alkoxy radical;

$R_2$ represents a $C_1$–$C_8$ straight- or branched-chain alkyl radical;

$R_4$ represents a $C_1$–$C_8$ straight- or branched-chain alkyl radical.

Among the $C_1$–$C_8$ straight- or branched-chain alkoxy radicals the following examples may be cited: methoxy; ethoxy; n-propoxy; isopropoxy; n-butoxy; isobutoxy; tert-butoxy; n-amyloxy; isoamyloxy; neopentyloxy; n-hexyloxy; n-heptyloxy and n-octyloxy.

Among the $C_1$–$C_8$ straight- or branched-chain alkyl radicals the following examples may be cited: methyl; ethyl; n-propyl; isopropyl; n-butyl; isobutyl; tert-butyl; n-amyl; isoamyl; neopentyl; n-hexyl; n-heptyl; n-octyl and 2-ethylhexyl.

Particularly preferred compounds of general formula (I) are:

1—Diethyl 4'-methoxybenzalmalonate
2—Diethyl 4'-tert-butoxybenzalmalonate
3—Diisopropyl 4'-methoxybenzalmalonate
4—Di-(2-ethylhexyl) 4'-methoxybenzalmalonate
5—Diethyl 4'-n-butoxy-3'-methoxybenzalmalonate
6—Diisopropyl 4'-n-butoxy-3'-methoxybenzalmalonate
7—Di-(2-ethylhexyl) 3',4'-dimethoxybenzalmalonate
8—Diisopropyl 3',4',5'-trimethoxybenzalmalonate
9—Diisoamyl 4'-methoxybenzalmalonate
10—Diethyl 4'-n-hexyloxybenzalmalonate The following dibenzoylmethane derivatives mentioned in the above patents may in particular be cited:
2-methyldibenzoylmethane
4-methyldibenzoylmethane
4-isopropyldibenzoylmethane
4-tert-butyldibenzoylmethane
2,4-dimethyldibenzoylmethane
2,5-dimethyldibenzoylmethane
4,4'-diisopropylbenzoylmethane
4-(1,1-dimethylethyl)-4'-methoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl-4-tert-butyl-4'-methoxydibenzoylmethane Among the dibenzoylmethane derivatives mentioned above, 4-(1,1-dimethylethyl)-4'-methoxydibenzoylmethane, sold by GIVAUDAN under the trade name "PARSOL 1789", and 4-isopropyl-dibenzoylmethane, sold by MERCK under the trade name "EUSOLEX 8020", are particularly preferred.

Dialkylbenzalmalonates nos. 1 to 10 above have the physicochemical characteristics shown in the following table:

| Compound No. | Appearance | Melting point | Boiling point | UV(ethanol)** $\lambda_{max}$ (nm) | $\epsilon_{max}$ (l · mol$^{-1}$cm$^{-1}$) |
|---|---|---|---|---|---|
| 1 | white powder | 40 | | 313 | 23 900 |
| 2 | pale yellow oil | | 163–7(13 Pa · s) | 304 | 20 600 |
| 3 | white powder | 45 | | 312 | 23 800 |
| 4 | colorless oil | | * | 313 | 23 000 |
| 5 | white powder | 60–1 | | 330 | 18 530 |
| | | | | 300(s) | 13 100 |
| 6 | white powder | 41 | | 329 | 19 700 |
| | | | | 300(s) | 13 600 |
| 7 | colorless oil | | * | 328 | 19 850 |
| | | | | 300(s) | 13 900 |
| 8 | colorless oil | 40–1 | 200 (104 Pa · s) | 311 | 17 680 |
| 9 | pale yellow oil | | 195 ( 13 Pa · s) | 312 | 24 000 |
| 10 | white powder | 33 | 190 ( 13 Pa · s) | 314 | 24 000 | s = shoulder
* = isolated using column chromatography
** = UV spectra have been obtained from ethanolic solutions containing the filter It can thus be seen that substituted dialkylbenzamalonates according to the invention are broad-band filters absorbing in the UV-B region (compounds 1,2,3,4,8,9 and 10) or both in the UV-A and UV-B regions (compounds 5,6 and 7).

One object of the invention is thus the use in cosmetics of substituted dialkylbenzalmalonates having formula (I) defined above as broad-band solar filters absorbing in the UV-A and UV-B regions to protect human skin against UV-A and UV-B radiation.

Compounds nos. 1 to 10 above are among those preferred. Those which are particularly preferred are compounds 5, 6 and 7, namely diethyl 4'-n-butoxy-3'-methoxybenzalmalonate, diisopropyl 4'-n-butoxy-3'-methoxybenzalmalonate and di-(2-ethylhexyl) 3',4'-dimethoxybenzalmalonate.

Dialkylbenzalmalonates are prepared by the standard Knoevenagel reaction, viz. condensation of an aromatic aldehyde with a malonic acid diester in toluene, in the presence of piperidinium acetate as catalyst. Water is eliminated by azeotropy. The reaction scheme is as follows:

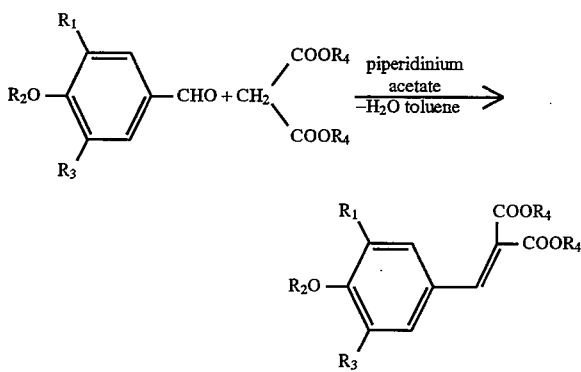

The products are recrystallized, distilled or separated using column chromatography.

Due to their liposolubility, the filters used distribute themselves uniformly in usual cosmetic support media containing at least one oily phase. Thus they may be applied to the skin to produce an effective protective film.

A further object of the invention is the provision of a photostable cosmetic composition which protects the skin against UV radiation at wavelengths between 280 and 380 nm, comprising, in an acceptable support medium containing at least one oily phase, 1 to 3% by weight of a dibenzoylmethane derivative and at least 1% by weight of a substituted dialkylbenzalmalonate having formula (I), the molar ratio of the compound having formula (I) to the dibenzoylmethane derivative being greater than or equal to 0.6.

Because of the solubilities of the compounds in the composition, this ratio is preferably less than or equal to 6. This upper limit is not critical, however.

A still further object of the invention is a method for protecting human skin against UV radiation at wavelengths between 280 and 380 nm consisting in applying a sufficient quantity of a cosmetic composition as hereinbefore defined to the skin.

Yet another object of the invention is constituted by a process for stabilizing dibenzoylmethane derivatives against UV radiation using a substituted dialkylbenzalmalonate having formula (I), using at least 1% by weight of said compound having formula (I) to stabilize 1 to 3% by weight of said dibenzoylmethane derivative, the molar ratio of said compound having formula (I) to said dibenzoylmethane derivative being greater than or equal to 0.6.

Some of the substituted dialkylbenzal- malonates having formula (I) are novel. Thus a further object of the invention is constituted by a novel compound having formula (I) selected from the following: diethyl 4'-tert-butoxybenzalmalonate; diisopropyl 4'-methoxybenzalmalonate; di-(2-ethylhexyl) 4'-methoxybenzalmalonate; diethyl 4'-n-butoxy-3'-methoxybenzalmalonate; diisopropyl 4'-n-butoxy-3'-methoxybenzalmalonate; di-(2-ethylhexyl) 3',4'-dimethoxybenzalmalonate; diisopropyl 3',4',5'-trimethoxybenzalmalonate, and diisoamyl 4'-methoxybenzalmalonate.

Because of the liposolubility of the dialkylbenzalmalonates having formula (I) and the dibenzoylmethane derivatives, cosmetic compositions according to the invention contain at least one oily phase. They may be produced in the form of oily or oleoalcoholic lotions, oily or oleoalcoholic gels, as solid sticks, as emulsions such as a cream or milk, or as an aerosol.

Oils or waxes, monoalcohols or lower polyols and mixtures thereof can be used as solubilizing solvents. Ethanol, isopropanol, propylene glycol and glycerine are particularly preferred monoalcohols or polyols.

A cosmetic composition according to the invention intended to protect human skin against ultraviolet radiation may contain any of the additives usual to this type of cosmetic composition, for example thickeners, emollients, humectants, surface-active agents, preservatives, antifoaming agents, oils, waxes, lanoline, perfumes, propellants, dyes and/or pigments to color either the composition itself or the skin, or any other ingredient in normal cosmetic use.

In one embodiment of the invention, an emulsion in the form of a cream or milk comprises, as well as a substituted dialkylmalonate associated, if desired, with a dibenzoylmethane derivative, fatty alcohols, fatty acid esters particularly fatty acid triglycerides, fatty acids, lanoline, natural or synthetic oils or waxes and emulsifiers, in the presence of water.

Oily lotions based on fatty acid esters, natural or synthetic oils and/or waxes, together with oleoalcoholic lotions based on oils or waxes, fatty acid esters such as fatty acid triglycerides and lower alcohols such as ethanol or glycols such as propylene glycol and/or polyols such as glycerine, constitute further embodiments of the invention.

Oleoalcoholic gels comprise oils or waxes lower alcohol or polyols such as ethanol, propylene glycol or glycerine, and a thickening agent such as silica.

Solid sticks are constituted by oily substances such as natural or synthetic oils or waxes, fatty alcohols, fatty acid esters and lanolin.

With an aerosol composition, standard propellants such as alkanes, fluoroalkanes and chlorofluoroalkanes may be used.

The following non-limiting examples are intended to illustrate the invention.

EXAMPLES

Example 1

Water-in-Oil Emulsion

| | |
|---|---|
| 4'-(1,1-dimethylethyl)-4'-methoxydibenzoylmethane (PARSOL 1789) | 1.5 g |
| Di-(2-ethylhexyl) 4'-methoxybenzalmalonate | 3.6 g |
| Mixture of cetylstearyl alcohol and cetylstearyl alcohol, oxyethylated with 33 moles of ethylene oxide | 7.3 g |
| Mixture of glycerol mono- and distearate | 2.1 g |
| $C_8$–$C_{12}$ fatty acid triglycerides | 31.4 g |
| Polydimethyl siloxane | 1.6 g |
| Cetyl alcohol | 1.6 g |
| Water qsp | 100 g |

This emulsion was prepared using standard techniques, by dissolving the filters in the oily phase containing the emulsifiers then heating this oily phase to around 80–85° C. and adding the water, previously heated to about 80° C., under vigorous agitation.

The stability of the "PARSOL 1789" was determined by spreading the emulsion as a 10 μm thick film between two quartz plates. The amount deposited was determined by weighing. The films were irradiated using a solar simulator.

After irradiation, the two quartz plates were separated and plunged into 5 ml of isopropanol, agitated for 30 minutes then filtered through a Millipore filter of 0.45 μm porosity. The amount of "PARSOL 1789" UV-A filter was then determined using high performance liquid chromatography.

After one hour's irradiation, there was only a small loss of "PARSOL 1789" in the emulsion containing the "PARSOL 1789"/di-(2-ethylhexyl) 4'-methoxybenzalmalonate combination compared with the loss of "PARSOL 1789" when combined with "PARSOL MCX", i.e. 2-ethylhexyl p-methoxycinnamate.

Example 2

Oily Lotion

The following ingredients were mixed together, and heated to 40–45° C. if necessary to homogenize:

| | |
|---|---|
| 4-(1,1-dimethylethyl) 4'-methoxydibenzoylmethane (PARSOL 1789) | 1.5 g |
| Di-(2-ethylhexyl) 3',4'-dimethoxybenzalmalonate | 4.5 g |
| Isopropyl myristate qsp | 100 g |

The test described in example 1 showed that the loss of "PARSOL 1789" in the presence of di-(2-ethylhexyl) 3',4'-dimethoxybenzalmalonate after one hour's irradiation was small compared with the loss of "PARSOL 1789" measured under the same conditions but in the presence of 2-ethylhexyl p-methoxycinnamate.

Example 3

Oily Lotion

The following ingredients were mixed together, and heated to 40–45° C. if necessary to homogenize:

| | |
|---|---|
| 4-(1,1-dimethylethyl) 4'-methoxydibenzoylmethane (PARSOL 1789) | 3 g |
| Diisoamyl 4'-methoxybenzalmalonate | 10 g |
| Isopropyl myristate qsp | 100 g |

The test described in example 1 showed that the loss of "PARSOL 1789" in the presence of diisoamyl 4'-methoxybenzalmalonate after one hour's irradiation was small compared with the loss of "PARSOL 1789" measured under the same conditions but in the presence of 2-ethylhexyl p-methoxycinnamate.

We claim:

1. A photostable cosmetic sunscreen composition for the protection of human skin against ultraviolet radiation at wavelengths between 280 and 380 nm consisting essentially of a cosmetically acceptable medium containing at least one oily phase; 1 to 3% by weight of a dibenzoylmethane derivative selected from the group consisting of 4-(1,1-dimethylethyl)-4'-methoxydibenzoylmethane and 4-isopropyldibenzoylmethane; and an effective amount for photostabilizing said dibenzoylmethane derivative of at least 1% by weight of a substituted dialkylbenzalmalonate having formula I:

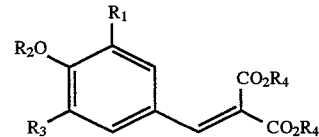

(I)

wherein:

$R_1$ and $R_3$ may be identical or different and represent a hydrogen atom or a $C_1$–$C_8$ straight- or branched-chain alkoxy radical;

$R_2$ represents a $C_1$–$C_8$ straight- or branched-chain alkyl radical; and $R_4$ represents a $C_1$–$C_8$ straight- or branched-chain alkyl radical, the molar ratio of said substituted dialkylbenzalmalonate having formula (I) to said dibenzoylmethane derivative being greater than or equal to 0.6.

2. A cosmetic sunscreen composition according to claim 1, wherein the molar ratio of said substituted dialkylbenzalmalonate having formula (I) to said dibenzoylmethane derivative is less than or equal to 6.

3. A cosmetic sunscreen composition according to claim 1, wherein said substituted dialkylbenzalmalonate is selected from the group consisting of:

diethyl 4'-methoxybenzalmalonate;
diethyl 4'-tert-butoxybenzalmalonate;
diisopropyl 4'-methoxybenzalmalonate;
di-(2-ethylhexyl) 4'-methoxybenzalmalonate;
diethyl 4'-n-butoxy-3'-methoxybenzalmalonate;
diisopropyl 4'-n-butoxy-3'-methoxybenzalmalonate;
di-(2-ethylhexyl) 3',4'-dimethoxybenzalmalonate;
diisopropyl 3',4',5'-trimethoxybenzalmalonate;
diisoamyl 4'-methoxybenzalmalonate, and
diethyl 4'-n-hexyloxybenzalmalonate.

4. A cosmetic sunscreen composition according to claim 1, in the form of an oily or oleoalcoholic lotion, an oily or oleoalcoholic gel, a solid stick, an emulsion or as an aerosol.

5. A cosmetic sunscreen composition according to claim 4, containing in addition, cosmetic additives selected from the group consisting of thickening agents, emollients, humectants, surface-active agents, preservatives, anti-foaming agents, perfumes, oils, waxes, lower monoalcohols or polyols, propellants, dyes and pigments.

6. A cosmetic sunscreen composition according to claim 4, in the form of a cream or milk emulsion, wherein the cosmetically acceptable medium comprises fatty alcohols, fatty acid esters particularly fatty acid triglyceride fatty acids, lanolin, natural or synthetic oils or waxes and emulsifiers, all in the presence of water.

7. A cosmetic sunscreen composition according to claim 4, in the form of an oily lotion, wherein the cosmetically acceptable medium comprises fatty acid esters, natural or synthetic oils and waxes.

8. A cosmetic sunscreen composition according to claim 4, in the form of an oleoalcoholic lotion, wherein the cosmetically acceptable medium comprises oils, waxes, fatty acid esters in particular fatty acid triglycerides and lower alcohols, glycols and polyols.

9. A cosmetic sunscreen composition according to claim 4, in the form of an oleoalcoholic gel, wherein the cosmetically acceptable medium comprises natural or synthetic oils or waxes, lower alcohols or polyols and a thickening agent.

10. In an improved cosmetic sunscreen composition for the protection of human skin against ultraviolet radiation at wavelengths between 280 and 380 nm comprising, in a cosmetically acceptable medium containing at least one oily phase, 1 to 3% by weight of a dibenzoylmethane derivative selected from the group consisting of 4-(1,1-dimethylethyl)-4'-methoxydibenzoylmethane and 4-isopropyldibenzoylmethane, wherein the improvement consists essentially of adding to said sunscreen cosmetic composition an effective amount for photostabilizing said dibenzoylmethane derivative of at least 1% by weight of a substituted dialkylbenzalmalonate having formula I:

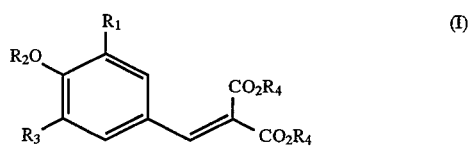

wherein:

$R_1$ and $R_3$ may be identical or different and represent a hydrogen atom or a $C_1$–$C_8$ straight- or branched-chain alkoxy radical;

$R_2$ represents a $C_1$–$C_8$ straight- or branched-chain alkyl radical; and $R_4$ represents a $C_1$–$C_8$ straight- or branched-chain alkyl radical, the molar ratio of said substituted dialkylbenzalmalonate of formula (I) to said dibenzoylmethane derivative being greater than or equal to 0.6.

11. A method of protecting human skin against UV radiation at wavelengths between 280 and 380 nm consisting in application to the skin of a sufficient quantity of a cosmetic sunscreen composition consisting essentially of a cosmetically acceptable medium containing at least one oily phase, 1 to 3% by weight of a dibenzoylmethane derivative selected from the group consisting of 4-(1,1-dimethylethyl)-4'-methoxydibenzoylmethane and 4-isopropyldibenzoylmethane, and an effective amount for photostabilizing said dibenzoylmethane derivative of at least 1% by weight of a substituted dialkylbenzalmalonate having formula I:

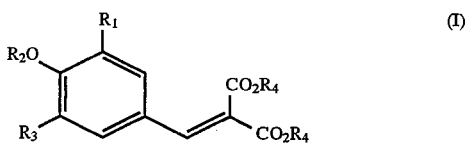

wherein:

$R_1$ and $R_3$ may be identical or different and represent a hydrogen atom or a $C_1$–$C_8$ straight- or branched-chain alkoxy radical;

$R_2$ represents a $C_1$–$C_8$ straight- or branched-chain alkyl radical; and $R_4$ represents a $C_1$–$C_8$ straight- or branched-chain alkyl radical, the molar ratio of said substituted dialkylbenzalmalonate having formula (I) to said dibenzoylmethane derivative being greater than or equal to 0.6.

* * * * *